United States Patent
Chang et al.

[11] Patent Number: 5,993,643
[45] Date of Patent: Nov. 30, 1999

[54] PROCESS FOR NAPHTHA HYDROCRACKING

[75] Inventors: Clarence D. Chang, Princeton; Scott Han, Lawrenceville; Roger A. Morrison, Lambertville, all of N.J.; Jose G. Santiesteban, Yardley, Pa.

[73] Assignee: Mobil Oil Corporation, Fairfax, Va.

[21] Appl. No.: 08/150,303

[22] Filed: Nov. 12, 1993

Related U.S. Application Data

[63] Continuation-in-part of application No. 08/095,884, Jul. 22, 1993, abandoned.

[51] Int. Cl.$^6$ ............................ C10G 11/04; C10G 65/00
[52] U.S. Cl. ............................ 208/59; 208/106; 208/107; 208/108; 208/112; 208/113
[58] Field of Search ............................ 208/59, 106, 107, 208/108, 112, 113

[56] References Cited

U.S. PATENT DOCUMENTS

| | | | |
|---|---|---|---|
| 3,755,147 | 8/1973 | Michalson | 208/112 |
| 3,923,641 | 12/1975 | Morrison | 208/111 |
| 4,283,272 | 8/1981 | Garwood et al. | 208/59 |
| 4,783,575 | 11/1988 | Schmidt et al. | 585/748 |
| 4,918,041 | 4/1990 | Hollstein et al. | 502/217 |
| 4,956,519 | 9/1990 | Hollstein et al. | 585/751 |
| 5,113,034 | 5/1992 | Soled et al. | 585/510 |

OTHER PUBLICATIONS

*Proceedings 9th International Congress on Catalysis*, vol. 4, 1727–1735 (1988), K. Arata and M. Hino.

Hino and Arata, "Synthesis of Solid Superacid of Tungsten Oxide Supported on Zirconia and Its Catalytic Action for Reactions of Butane and Pentane", J. Chem. Soc., Chem. Commun., 1259–1260 (1988) No month available.

*Primary Examiner*—Elizabeth D Wood
*Attorney, Agent, or Firm*—Lori F. Cuomo; Dennis P. Santini

[57] ABSTRACT

There is provided a hydrocracking process using a catalyst comprising a hydrogenation/dehydrogenation component, such as a noble metal, and an acidic solid component comprising a Group IVB metal oxide modified with an oxyanion of a Group VIB metal. An example of this catalyst is zirconia, modified with tungstate and platinum. This catalyst is used to selectively hydrocrack naphtha range hydrocarbons to reduce the endpoint of reformulated gasolines.

22 Claims, No Drawings

PROCESS FOR NAPHTHA HYDROCRACKING

CROSS-REFERENCE TO RELATED APPLICATIONS

This application is a continuation-in-part of application Ser. No. 08/095,884, filed Jul. 22, 1993 and now abandoned, entitled "Paraffin Isomerization Catalyst and Process for Its Use," incorporated herein in its entirety by reference. This application is further related by subject matter to co-pending application Ser. No. 08/150,304 filed Nov. 12, 1993 entitled "A Process For Selective Wax Hydrocracking".

FIELD OF THE INVENTION

The present invention relates to a process for hydrocracking naphtha using a catalyst. More particularly, the invention relates to a process for enhancing naphtha hydrocracking to reduce the endpoint of reformulated gasolines.

BACKGROUND OF THE INVENTION

One of the processing challenges for producing reformulated gasoline is endpoint reduction. Lowering gasoline endpointo,as been reported to reduce pollution. A specification of 90% of the gasoline boils below 300° F. has been proposed for California.

Zeolite beta has been found particularly well-suited for use in a catalyst for hydrocracking naphtha under mild conditions. U.S. Pat. No. 3,923,641 to Morrison, discloses that $C_5+$ naphtha can be readily upgraded to a product which contains increased amounts of isobutane relative to n-butane, by hydrocracking the naphtha over zeolite beta. There is no disclosure of endpoint reduction in gasolines.

It has now been found that a $C_5+$ naphtha, e.g., $C_6+$ or $C_7+$ naphtha can be hydrocracked by a process which comprises contacting the naphtha with a catalyst composition comprising a hydrogenation/dehydrogenation component and an acidic solid component comprising a Group IVB metal oxide modified with an oxyanion of a Group VIB metal.

In the present invention a catalyst composition comprising a hydrogenation/dehydrogenation component and an acidic solid component comprising a Group IVB metal oxide modified with an oxyanion of a Group VIB metal is found to be selective for naphtha hydrocracking to reduce the endpoint of reformulated gasolines. The endpoint is lowered through selective hydrocracking of the $C_{10}+$ fraction.

SUMMARY

There is provided a process for hydrocracking naphtha, said process comprising contacting a naphtha feed with a hydrocracking catalyst under sufficient hydrocracking conditions, said hydrocracking catalyst comprising a hydrogenation/dehydrogenation component and an acidic solid component comprising a Group IVB metal oxide modified with an oxyanion of a Group VIB metal.

Processing a pretreated naphtha reformer feed over the catalyst of the present invention results in up to 99+% conversion of $C_{10}+$ feed components with substantial $C_{13}+$ conversion. The 90% at 300° F. specification may be met under the process of the present invention.

As used herein, the term naphtha is intended to mean a petroleum cut having a boiling range within about $C_5$ to 425° F. (about 218° C.).

The naphtha feedstock can be treated prior to hydrocracking in order to reduce or substantially eliminate its heteroatom content. As necessary or desired, the feedstock can be hydrotreated under mild or moderate hydroprocessing conditions to reduce its sulfur, nitrogen, oxygen and metal content. The mild to moderate hydrotreating conditions employed include pressures of from about 2 to about 21 MPa and $H_2$ consumptions of from about 20 to about 280 $m^3/m^3$. Conventional hydrotreating process conditions and catalysts can be employed, e.g., those described in U.S. Pat. No. 4,283,272, the contents of which are incorporated by reference herein.

EMBODIMENTS

The catalyst described herein comprises an oxide of a Group IVB metal, preferably zirconia or titania. This Group IVB metal oxide is modified in two ways. According to one modification, the Group IVB metal oxide is modified with an oxyanion of a Group VIB metal, such as an oxyanion of tungsten, such as tungstate. The modification of the Group IVB metal oxide with the oxyanion of the Group VIB metal imparts acid functionality to the material. The modification of a Group IVB metal oxide, particularly, zirconia, with a Group VIB metal oxyanion, particularly tungstate, is described in U.S. Pat. No. 5,113,034; in Japanese Kokai Patent Application No. Hei 1 [1989]-288339; and in an article by K. Arata and M. Hino in *Proceedings 9th International Congress on Catalysis*, 4, 1727–1735 (1988), the entire disclosures of these publications are expressly incorporated herein by reference.

According to another modification of the Group IVB metal oxide described herein, a hydrogenation/dehydrogenation component is combined with the Group IV metal oxide. This hydrogenation/dehydrogenation component imparts the ability of the material to catalyze the addition of hydrogen to or the removal of hydrogen from organic compounds, such as hydrocarbons, optionally substituted with one or more heteroatoms, such as oxygen, nitrogen, metals or sulfur, when the organic compounds are contacted with the modified material under sufficient hydrogenation or dehydrogenation conditions.

Examples of hydrogenation/dehydrogenation components include the oxide, hydroxide or free metal (i.e., zero valent) forms of Group VIII metals (i.e., Pt, Pd, Ir, Rh, Os, Ru, Ni, Co and Fe), Group IVA metals (i.e., Sn and Pb), Group VB metals (i.e., Sb and Bi) and Group VIIB metals (i.e., Mn, Tc and Re). The present catalyst preferably comprises one or more catalytic forms of one or more noble metals (i.e., Pt, Pd, Ir, Rh, Os or Ru). Combinations of catalytic forms of such noble or non-noble metals, such combinations of Pt with Sn, may be used. The valence state of the metal of the hydrogenation/dehydrogenation component is preferably in a reduced valance state, e.g., when this component is in the form of an oxide or hydroxide. The reduced valence state of this metal may be attained, in situ, during the course of a reaction, when a reducing agent, such as hydrogen, is included in the feed to the reaction.

For the purposes of the present disclosure, the expression, Group IVB metal oxide modified with an oxyanion of a Group VIB metal, is intended to connote a material comprising, by elemental analysis, a Group IVB metal, a Group VIB metal and oxygen, with more acidity than a simple mixture of separately formed Group IVB metal oxide mixed with a separately formed Group VIB metal oxide or oxyanion. The present Group IVB metal, e.g., zirconium, oxide modified with an oxyanion of a Group VIB metal, e.g., tungsten, is believed to result from an actual chemical interaction between a source of a Group IVB metal oxide and a source of a Group VIB metal oxide or oxyanion.

This chemical interaction is discussed in the aforementioned article by K. Arata and M. Hino in *Proceedings 9th International Congress on Catalysis*, 4, 1727–1735 (1988). In this article, it is suggested that solid superacids are formed when sulfates are reacted with hydroxides or oxides of certain metals, e.g., Zr. These superacids are said to have the structure of a bidentate sulfate ion coordinated to the metal, e.g., Zr. In this article, it is further suggested that a superacid can also be formed when tungstates are reacted with hydroxides or oxides of Zr. The resulting tungstate modified zirconia materials are theorized to have an analogous structure to the aforementioned superacids comprising sulfate and zirconium, wherein tungsten atoms replace sulfur atoms in the bidentate structure.

Although it is believed that the present catalysts may comprise the bidentate structure suggested in the aforementioned article by Arata and Hino, the particular structure of the catalytically active site in the present Group IVB metal oxide modified with an oxyanion of a Group VIB metal has not yet been confirmed, and it is not intended that this catalyst component should be limited to any particular structure.

Other elements, such as alkali (Group IA) or alkaline earth (Group IIA) compounds may optionally be added to the present catalyst to alter catalytic properties. The addition of such alkali or alkaline earth compounds to the present catalyst may enhance the catalytic properties of components thereof, e.g., Pt or W, in terms of their ability to function as a hydrogenation/dehydrogenation component or an acid component.

The Group IVB metal (i.e., Ti, Zr or Hf) and the Group VIB metal (i.e., Cr, Mo or W) species of the present catalyst are not limited to any particular valence state for these species. These species may be present in this catalyst in any possible positive oxidation value for these species. Subjecting the catalyst, e.g., when the catalyst comprises tungsten, to reducing conditions, e.g., believed to be sufficient to reduce the valence state of the tungsten, may enhance the overall catalytic ability of the catalyst to catalyze certain reactions, e.g., the isomerization of n-hexane.

Suitable sources of the Group IVB metal oxide, used for preparing the present catalyst, include compounds capable of generating such oxides, such as oxychlorides, chlorides, nitrates, etc., particularly of zirconium or titanium. Alkoxides of such metals may also be used as precursors or sources of the Group IVB metal oxide. Examples of such alkoxides include zirconium n-propoxide and titanium i-propoxide. Preferred sources of a Group IVB metal oxide are zirconium hydroxide, i.e., $Zr(OH)_4$, and hydrated zirconia. The expression, hydrated zirconia, is intended to connote materials comprising zirconium atoms covalently linked to other zirconium atoms via bridging oxygen atoms, i.e., Zr—O—Zr, further comprising available surface hydroxy groups. These available surface hydroxyl groups are believed to react with the source of an anion of a Group IVB metal, such as tungsten, to form the present acidic catalyst component. As suggested in the aforementioned article by K. Arata and M. Hino in *Proceedings 9th International Congress on Catalysis*, 4, 1727–1735 (1988), precalcination of $Zr(OH)_4$ at a temperature of from about 100° C. to about 400° C. results in a species which interacts more favorably with tungstate. This precalcination is believed to result in the condensation of ZrOH groups to form a polymeric zirconia species with surface hydroxyl groups. This polymeric species is referred to herein as a form of a hydrated zirconia.

Treatment of hydrated zirconia with a base solution prior to contact with a source of tungstate may be preferable. More particularly, as demonstrated in Examples recited hereinafter, especially in Examples 16–25, refluxing hydrated zirconia in an $NH_4OH$ solution having a pH of greater than 7 was beneficial. Without wishing to be bound by any theory, it is theorized that the base-treated, hydrated zirconia is better because it has higher surface area. It is also theoretically possible that the base treatment alters surface hydroxyl groups on the hydrated zirconia, possibly in a manner which promotes a more desirable interaction with the source of tungstate later used.

Suitable sources for the oxyanion of the Group VIB metal, preferably molybdenum or tungsten, include, but are not limited to, ammonium metatungstate or metamolybdate, tungsten or molybdenum chloride, tungsten or molybdenum carbonyl, tungstic or molybdic acid and sodium tungstate or molybdate.

The hydrogenation/dehydrogenation component of the present catalyst may be derived from Group VIII metals, such as platinum, iridium, osmium, palladium, rhodium, ruthenium, nickel, cobalt, iron and mixtures of two or more thereof. These components may optionally be mixed with components derived from Group IVA metals, preferably Sn, and/or components derived from Group VIIB metals, preferably rhenium and manganese. These components may be added to the catalyst by methods known in the art, such as ion exchange, impregnation or physical admixture. For example, salt solutions of these metals may be contacted with the remaining catalyst components under conditions sufficient to combine the respective components. The metal containing salt is preferably water soluble. Examples of such salts include chloroplatinic acid, tetraammineplatinum complexes, platinum chloride, tin sulfate and tin chloride.

The present catalyst may be prepared, for example, by impregnating the hydroxide or oxide, particularly the hydrated oxide, of the Group IVB metal with an aqueous solution containing an anion of the Group VIB metal, preferably tungstate or molybdate, followed by drying. Calcination of the resulting material may be carried out, preferably in an oxidizing atmosphere, at temperatures from about 500° C. to about 900° C., preferably from about 700° C. to about 850° C., and more preferably from about 750° C. to about 825° C. The calcination time may be up to 48 hours, preferably for about 0.5–24 hours, and more preferably for about 1.0–10 hours. In a most preferred embodiment, calcination is carried out at about 800° C. for about 1 to about 3 hours. The hydrogenation/dehydrogenation component of the catalyst (e.g., Group VIII metal, Group VIIB metal, etc.) may be added after or before the calcination step by techniques known in the art, such as impregnation, coimpregnation, coprecipitation, physical admixture, etc. The hydrogenation/dehydrogenation component may also be combined with the remaining catalyst components before or after these remaining components are combined with a binder or matrix material as described hereinafter.

When a source of the hydroxide or hydrated oxide of zirconium is used, calcination, e.g., at temperatures greater than 500° C., of the combination of this material with a source of an oxyanion of tungsten may be needed to induce the theorized chemical reaction which imparts the desired degree of acidity to the overall material. However, when more reactive sources of zirconia are used, it is possible that such high calcination temperature may not be needed.

In the present catalyst, of the Group IVB oxides, zirconium oxide is preferred; of the Group VIB anions, tungstate is preferred; and of the hydrogenation/dehydrogenation components, platinum and/or platinum-tin are preferred.

Qualitatively speaking, elemental analysis of the present catalyst will reveal the presence of Group IVB metal, Group VIB metal and oxygen. The amount of oxygen measured in such an analysis will depend on a number of factors, such as the valence state of the Group IVB and Group VIB metals, the form of the hydrogenation/dehydrogenation component, moisture content, etc. Accordingly, in characterizing the composition of the present catalyst, it is best not to be restricted by any particular quantities of oxygen. In functional terms, the amount of Group VIB oxyanion in the present catalyst may be expressed as that amount which increases the acidity of the Group IVB oxide. This amount is referred to herein as an acidity increasing amount. Elemental analysis of the present catalyst may be used to determine the relative amounts of Group IVB metal and Group VIB metal in the catalyst. From these amounts, mole ratios in the form of $XO_2/YO_3$ may be calculated, where X is said Group IVB metal, assumed to be in the form $XO_2$, and Y is said Group VIB metal, assumed to be in the form of $YO_3$. It will be appreciated, however, that these forms of oxides, i.e., $XO_2$ and $YO_3$, may not actually exist, and are referred to herein simply for the purposes of calculating relative quantities of X and Y in the present catalyst. The present catalysts may have calculated mole ratios, expressed in the form of $XO_2/YO_3$, where X is at least one Group IVB metal (i.e., Ti, Zr, and Hf) and Y is at least one Group VIB metal (i.e., Cr, Mo, or W), of up to 1000, e.g., up to 300, e.g., from 2 to 100, e.g., from 4 to 30.

The amount of hydrogenation/dehydrogenation component may be that amount which imparts or increases the catalytic ability of the overall material to catalytically hydrogenate or dehydrogenate a hydrogenatable or dehydrogenatable organic compound under sufficient hydrogenation or dehydrogenation conditions. This amount is referred to herein as a catalytic amount. Quantitatively speaking, the present catalyst may comprise, for example, from about 0.001 to about 5 wt %, e.g., from about 0.1 to about 2 wt %, of the hydrogenation/dehydrogenation component, especially when this component is a noble metal.

It may be desirable to incorporate the present catalyst with another material to improve its properties. Such materials include active and inactive materials and synthetic or naturally occurring zeolites as well as inorganic materials such as clays, silica, and/or metal oxides. The latter may be either naturally occurring or in the form of gelatinous precipitates, sols, or gels including mixtures of silica and metal oxides.

The present catalyst includes a hydrogenation-dehydrogenation component to the catalyst. Metals having a strong hydrogenation function are preferred, especially platinum and the other noble metals such as palladium, rhodium, iridium, rhenium, although other metals capable of acting as a hydrogenation component may also be used, for example, nickel, tungsten or other metals of Group VIIIA of the Periodic Table (IUPAC Table), either singly, in mixtures or in combination with other metals. The amount of the noble metal component may be in the range 0.001 to 5 wt. % of the total catalyst, e.g., from 0.1 to 2 wt. %. Base metal hydrogenation components may be added in somewhat greater amounts. The hydrogenation component can be exchanged onto the support material, impregnated into it or physically admixed with it. If the metal is to be impregnated into or exchanged onto the support, it may be done, for example, by treating the support with a platinum metal-containing ion. Suitable platinum compounds include chloroplatinic acid, platinous chloride and various compounds containing the platinum ammine complex. The metal compounds may be either compounds in which the metal is present in the cation or anion of the compound; both types of compounds can be used. Platinum compounds in which the metal is in the form of a cation of cationic complex, e.g., $Pt(NH_3)_4Cl_2$ are particularly useful, as are anionic complexes such as the vanadate and metatungstate ions. Cationic forms of other metals are also useful since they may be exchanged onto the support or impregnated into it.

The catalyst may be subjected to a final calcination under conventional conditions in order to convert the metal component to the oxide form and to confer the required mechanical strength on the catalyst. Prior to use the catalyst may be subjected to presulfiding.

When a source of hydrogenation metal, such as $H_2PtCl_6$, is used as a source of a hydrogenation-dehydrogenation component in the present catalyst, it may be desirable to subject the present catalyst to extended reducing conditions, e.g., lasting more than 4 hours.

The hydrocracking process using the catalyst of the present invention can be run under a variety of conditions. The pressure may vary from 0 to about 2,000 psig, but will preferably be from about 200 to about 800 psig. The temperature of reaction is preferably from about 450° F. to about 550° F. but may range from about 400° F. to about 650° F. The hydrogen to hydrocarbon ratio, in a mole basis, can run from about 1 to 1 to about 15 to 1, preferably from about 3 to 1 to about 7 to 1. Weight hourly space velocities (WHSV) may be from about 0.5 to about 20, preferably from about 1 to about 3.

The following examples illustrate the process of the present invention.

Catalyst A

A $Pt/WO_x/ZrO_2$ catalyst was prepared by impregnating ammonium metatungstate (17.5 wt. % W target loading) on hydrous zirconia. The hydrous zirconia was prepared by dissolving $ZrOCl_2$ in water, precipitating out with $NH_4OH$, and subsequent overnight refluxing of the precipitate in water set to pH~9 with $NH_4OH$. After W impregnation, the catalyst was calcined at 825° C. in air for 3 hours. Platinum was then impregnated onto the catalyst with $H_2PtCl_6$ solution (0.5 wt. % Pt target loading) and the final catalyst calcined at 300° C. in air for 3 hours. In the catalytic tests, Catalyst A was reduced in $H_2$ (100 cc/min) at 100 psig and 900° F. overnight.

Catalyst B

A $Pt/WO_xZrO_2$ catalyst was prepared by impregnating ammonium metatungstate (1 part W per 2.2 parts water) on hydrous zirconia (7.5 parts) precipitated from $ZrOCl_2$ and $NH_4OH$. This catalyst was then calcined at 800° C. for 2 hours in flowing air. Pt was impregnated using $H_2PtCl_6$ solution (0.5 wt. % Pt target loading) and the resultant catalyst calcined at 350° C. in flowing air for 3 hours. In the catalytic tests, Catalyst B was reduced in $H_2$ (100 cc/min) at 100 psig and 900° F. for 2 hours.

Catalyst A and Catalyst B were tested with a pretreated naphtha reformer feed. Pretreatment conditions employed were approximately 570° F., 680 psig, 1.5 WHSV and 3000 SCF/B $H_2$ circulation. The feed composition and reaction conditions are given in Tables 1 and 2. The catalytic results are given in Table 3. At lower pressures (200–400 psig) Catalyst A showed selectivity for conversion of $C_{10}+$ and $C_{13}+$ feed components. Conversion of up to 80 wt. % $C_{10}$'s and 77 wt. % $C_{13}$'s was achieved using Catalyst A. Run 3 from Table 1 shows a 304° F. endpoint was obtained at the 90% distillation point using Catalyst A. Catalyst B, tested at 800 psig, showed significant activity for endpoint reduction. From the higher conversions with Catalyst B it is believed that greater reductions in endpoint are possible.

TABLE 1

Feed Composition

| Product Dist., wt. % | |
|---|---|
| $C_1$ | |
| $C_2$ | |
| $C_2=$ | |
| $C_3$ | |
| $C_3=$ | |
| $i-C_4$ | 0.01 |
| $n-C_4$ | 0.08 |
| $C_4=$ | 0.02 |
| $i-C_5$ | 1.60 |
| $n-C_5$ | 1.73 |
| $C_5=$ | — |
| 2,2 dimethyl-$C_4$ | 0.04 |
| Cyclo-$C_5$ | 0.34 |
| 2,3 dimethyl-$C_4$ | 0.30 |
| 2-methyl-$C_5$ | 2.36 |
| 3-methyl-$C_5$ | 1.31 |
| $n-C_6$ | 2.39 |
| $C_6=$ | — |
| methyl-cyclo-$C_5$ | 2.23 |
| Benzene | 0.24 |
| Cyclo-$C_6$ | 0.89 |
| $C_7$'s | 17.94 |
| $n-C_7$ | 3.19 |
| Toluene | — |
| $C_8$'s | 16.97 |
| $n-C_8$ | 3.72 |
| $C_9$'s | 19.08 |
| $n-C_9$ | 3.36 |
| $C_{10}$'s | 12.07 |
| $n-C_{10}$ | 4.08 |
| $C_{11}$'s | 4.00 |
| $n-C_{11}$ | 1.51 |
| $C_{12}$'s | 0.37 |
| $n-C_{12}$ | 0.08 |
| $C_{13}+$'s | 0.09 |
| Temp. ° F. for 90% dist. | 337.00 |

TABLE 2

Reaction Conditions

| Run No. | 1 | 2 | 3 | 4 | 5 |
|---|---|---|---|---|---|
| Catalyst | A | A | A | B | B |
| Temp, ° F. | 499 | 550 | 550 | 499 | 600 |
| Pressure, psig | 200 | 400 | 400 | 800 | 800 |
| WHSV, hr$^{-1}$ | 0.43 | 0.43 | 0.43 | 0.38 | 0.41 |
| $H_2$/hydrocarbon | 4/1 | 4/1 | 4/1 | 4/1 | 4/1 |

TABLE 3

| Run No. | 1 | 2 | 3 | 4 | 5 |
|---|---|---|---|---|---|
| Product Dist., wt. % | | | | | |
| $C_1$ | 0.00 | 0.00 | 0.00 | 0.00 | 0.11 |
| $C_2$ | 0.00 | 0.02 | 0.03 | 0.01 | 0.18 |
| $C_2=$ | 0.00 | 0.00 | 0.00 | 0.00 | 0.00 |
| $C_3$ | 0.13 | 0.64 | 0.94 | 1.00 | 8.26 |
| $C_3=$ | 0.00 | 0.00 | 0.00 | 0.00 | 0.00 |
| $i-C_4$ | 0.95 | 4.25 | 6.21 | 8.87 | 24.22 |
| $n-C_4$ | 0.19 | 0.71 | 1.10 | 1.15 | 7.22 |
| $C_4=$ | 0.00 | 0.00 | 0.00 | 0.00 | 0.00 |
| $i-C_5$ | 2.04 | 4.09 | 5.83 | 6.72 | 14.21 |
| $n-C_5$ | 1.47 | 1.57 | 1.67 | 1.90 | 5.51 |

TABLE 3-continued

| Run No. | 1 | 2 | 3 | 4 | 5 |
|---|---|---|---|---|---|
| $C_5=$ | 0.00 | 0.00 | 0.00 | 0.00 | 0.00 |
| 2,2 dimethyl-$C_4$ | 0.04 | 0.04 | 0.05 | 0.10 | 1.03 |
| Cyclo-$C_5$ | 0.30 | 0.25 | 0.41 | 0.41 | 0.51 |
| 2,3 dimethyl-$C_4$ | 0.39 | 0.57 | 0.56 | 0.63 | 1.21 |
| 2-methyl-$C_5$ | 2.74 | 3.38 | 3.94 | 4.30 | 5.45 |
| 3-methyl-$C_5$ | 1.50 | 1.82 | 2.12 | 2.64 | 3.63 |
| $n-C_6$ | 2.51 | 2.49 | 2.50 | 2.34 | 2.87 |
| $C_6=$ | 0.00 | 0.00 | 0.00 | 0.00 | 0.00 |
| methyl-cyclo-$C_5$ | 2.79 | 4.05 | 5.02 | 6.44 | 5.21 |
| Benzene | 0.41 | 0.40 | 0.42 | 0.00 | 0.00 |
| Cyclo-$C_6$ | 0.96 | 0.98 | 1.05 | 1.58 | 1.16 |
| $C_7$'s | 21.50 | 22.72 | 23.59 | 24.42 | 12.99 |
| $n-C_7$ | 3.48 | 3.23 | 3.10 | 2.34 | 0.98 |
| Toluene | 0.00 | 0.00 | 0.00 | 0.00 | 0.00 |
| $C_8$'s | 18.14 | 18.91 | 18.77 | 21.88 | 3.73 |
| $n-C_8$ | 3.97 | 4.11 | 4.03 | 2.90 | 0.56 |
| $C_9$'s | 18.07 | 14.80 | 11.82 | 7.66 | 0.62 |
| $n-C_9$ | 3.15 | 2.97 | 2.53 | 1.57 | 0.11 |
| $C_{10}$'s | 8.64 | 4.89 | 2.45 | 0.78 | 0.18 |
| $n-C_{10}$ | 2.78 | 1.91 | 1.18 | 0.26 | 0.00 |
| $C_{11}$'s | 1.96 | 0.42 | 0.37 | 0.10 | 0.02 |
| $n-C_{11}$ | 1.11 | 0.62 | 0.27 | 0.00 | 0.00 |
| $C_{12}$'s | 0.60 | 0.09 | 0.02 | 0.01 | 0.00 |
| $n-C_{12}$ | 0.07 | 0.03 | 0.01 | 0.00 | 0.00 |
| $C_{13}+$'s | 0.12 | 0.04 | 0.02 | 0.01 | 0.00 |
| Wt % conv, total | 8.72 | 19.13 | 26.15 | 36.23 | 67.52 |
| Wt. % conv, $C_{10}+$'s | 32.34 | 63.96 | 80.57 | 94.78 | 99.06 |
| Wt. % conv, | | | | | |
| $C_{10}$'s. | 28.40 | 59.51 | 79.73 | 93.58 | 98.47 |
| $n-C_{10}$ | 31.92 | 53.29 | 71.13 | 93.65 | 100.00 |
| $C_{11}$'s | 44.35 | 81.01 | 88.38 | 98.15 | 99.61 |
| $C_{12}$'s | — | 73.81 | 93.36 | 96.48 | 99.46 |
| $C_{13}+$'s | — | 51.24 | 77.86 | 93.78 | 100.00 |
| Wt % $C_1-C_4$ made | 1.18 | 5.53 | 8.19 | 10.94 | 39.91 |
| $i-C_4/n-C_4$ | 4.99 | 5.96 | 5.66 | 7.75 | 3.35 |
| $i-C_4/(C_1-C_4) \times 100$ | 80.69 | 76.91 | 75.88 | 81.13 | 60.69 |
| ~$H_2$ consumed, SCF/B | 308.00 | 406.00 | 512.00 | 719.00 | 1422.00 |
| Temp., ° F. for 90% dist. | 322 | 313 | 304 | — | — |

Changes and modifications in the specifically described embodiments can be carried out without departing from the scope of the invention which is intended to be limited only by the scope of the appended claims.

What is claimed is:

1. A process for hydrocracking naphtha, said process comprising contacting a naphtha feed with a hydrocracking catalyst under sufficient hydrocracking conditions, said hydrocracking catalyst comprising a hydrogenation/dehydrogenation catalytic component and an acidic solid catalytic component comprising a Group IVB metal oxide modified with an oxyanion of a Group VIB metal.

2. A process according to claim 1, wherein said hydrogenation/dehydrogenation component comprises a noble metal.

3. A process according to claim 2, wherein said hydrogenation/dehydrogenation component, in addition to said noble metal, further comprises at least one non-noble metal in the form of at least one oxide, hydroxide or metal of at least one element selected from the group consisting of Group VIII metals, Group IVA metals, Group VB metals and Group VIIB metals.

4. A process according to claim 1, wherein said hydrogenation/dehydrogenation component comprises platinum.

5. A process according to claim 2, wherein said hydrogenation/dehydrogenation component further comprises tin.

6. A process according to claim 1, wherein said Group IVB metal oxide comprises zirconia or titania.

7. A process according to claim 1, wherein said Group VIB metal oxyanion is an oxyanion of molybdenum or tungsten.

8. A process according to claim 1, wherein said hydrogenation/dehydrogenation component comprises platinum in the form of an oxide, hydroxide or free metal, said Group IVB metal oxide is zirconium oxide, and said Group VIB metal dxyanion is tungstate.

9. A process according to claim 1, wherein said catalyst comprises a calculated mole ratio of $XO_2/YO_3$, where X is said Group IVB metal and Y is said Group VIB metal, of up to 300 and from 0.001 wt % to about 5 wt % of said hydrogenation/dehydrogenation component, based upon the total weight of the catalyst.

10. A process according to claim 8, wherein said catalyst comprises a calculated mole ratio of $XO_2/YO_3$, where X is said Group IVB metal and Y is said Group VIB metal, of from 2 to 100 and from 0.001 wt % to about 5 wt % of said hydrogenation/dehydrogenation component, based upon the total weight of the catalyst.

11. A process according to claim 8, wherein said catalyst comprises a calculated mole ratio of $XO_2/YO_3$, where X is said Group IVB metal and Y is said Group VIB metal, of from 4 to 30 and from 0.1 wt % to about 2 wt % of platinum, based upon the total weight of the catalyst.

12. A process according to claim 1, wherein said contacting is in the presence of hydrogen.

13. A process according to claim 12, wherein said hydrocracking conditions include a temperature from about 400° F. to about 650° F., a pressure of about 0 to about 2000 psig, a molar ratio of hydrogen to hydrocarbon of from 0.1 to 1 to about 15 to 1, and a weight hourly space velocity of about 0.1 to about 20.

14. A process according to claim 13, wherein said temperature is from about 450° F. to about 550° F.

15. A process according to claim 14, wherein said pressure is from about 200 to about 800 psig.

16. A process according to claim 15, wherein said molar ratio of hydrogen to hydrocarbon is from about 3 to 1 to about 7 to 1.

17. A process according to claim 16, wherein said weight hourly space velocity is from about 0.2 to about 3.

18. A process for the endpoint reduction of gasoline, said process comprising contacting a naphtha feed having a $C_{10}+$ fraction with a hydrocracking catalyst under sufficient hydrocracking conditions to selectively hydrocrack the $C_{10}+$ fraction, said hydrocracking catalyst comprising a hydrogenation/dehydrogenation catalytic component and an acidic solid catalytic component comprising a Group IVB metal oxide modified with an oxyanion of a Group VIB metal.

19. A process according to claim 18 wherein the endpoint is reduced to 90% at 300° F.

20. A process according to claim 1, wherein said Group IVB metal oxide is modified with an acidity increasing amount of said oxyanion of a Group VIB metal.

21. A process according to claim 18, wherein said Group IVB metal oxide is modified with an acidity increasing amount of said oxyanion of a Group VIB metal.

22. A process for hydrocracking naptha, said process comprising contacting a naptha feed with a hydrocracking catalyst under sufficient hydrocracking conditions, said hydrocracking catalyst comprising a hydrogenation/dehydrogenation component and an acidic solid component comprising a Group IVB metal oxide modified with an oxyanion of a Group VIB metal, wherein said catalyst is prepared by reacting the oxyanion of the Group VIB metal with a hydroxide or oxide of a Group IVB metal and calcining at a temperature in the range of from about 500° C. to about 900° C.

* * * * *

UNITED STATES PATENT AND TRADEMARK OFFICE
CERTIFICATE OF CORRECTION

PATENT NO. : 5,993,643
DATED : November 30, 1999
INVENTOR(S) : Clarence D. CHANG et al.

It is certified that error appears in the above-identified patent and that said Letters Patent is hereby corrected as shown below:

Claim 8, column 9, line 8, "dxyanion" should read ---oxyanion---.

Signed and Sealed this

Thirteenth Day of March, 2001

Attest:

NICHOLAS P. GODICI

Attesting Officer     Acting Director of the United States Patent and Trademark Office